(12) United States Patent
Noo

(10) Patent No.: US 9,495,770 B2
(45) Date of Patent: Nov. 15, 2016

(54) PRACTICAL MODEL BASED CT CONSTRUCTION

(71) Applicant: University of Utah Research Foundation, Salt Lake City, UT (US)

(72) Inventor: Frederic Noo, Salt Lake City, UT (US)

(73) Assignee: University of Utah Research Foundation, Salt Lake City, UT (US)

(*) Notice: Subject to any disclaimer, the term of this patent is extended or adjusted under 35 U.S.C. 154(b) by 7 days.

(21) Appl. No.: 14/460,172

(22) Filed: Aug. 14, 2014

(65) Prior Publication Data
US 2015/0078506 A1   Mar. 19, 2015

Related U.S. Application Data

(60) Provisional application No. 61/865,721, filed on Aug. 14, 2013.

(51) Int. Cl.
A61B 6/00 (2006.01)
G06T 11/00 (2006.01)
A61B 6/03 (2006.01)

(52) U.S. Cl.
CPC ............ *G06T 11/003* (2013.01); *G06T 11/006* (2013.01); *A61B 6/032* (2013.01); *G06T 2211/421* (2013.01); *G06T 2211/424* (2013.01)

(58) Field of Classification Search
CPC ...... A61B 6/032; A61B 6/5205; A61B 6/03; A61B 6/5258; G01N 23/04
See application file for complete search history.

(56) References Cited

U.S. PATENT DOCUMENTS

| 8,005,287 | B2* | 8/2011 | Grasruck | G60T 11/006 378/4 |
| 8,416,914 | B2 | 4/2013 | Thibault et al. | |
| 8,532,350 | B2 | 9/2013 | Fahimian et al. | |
| 2005/0105694 | A1* | 5/2005 | Brandt | G06T 11/006 378/210 |
| 2009/0279768 | A1* | 11/2009 | Nishikawa | A61B 6/032 382/132 |
| 2011/0243417 | A1* | 10/2011 | Madabhushi | G06K 9/3233 382/131 |
| 2012/0155728 | A1 | 6/2012 | DeMan et al. | |
| 2012/0201442 | A1* | 8/2012 | Beck | A61B 6/032 382/131 |
| 2013/0343672 | A1 | 12/2013 | Yu et al. | |
| 2013/0343673 | A1 | 12/2013 | Pal et al. | |
| 2014/0334705 | A1* | 11/2014 | Ishii | A61B 6/032 382/131 |

OTHER PUBLICATIONS

Chang et al.; "Assessment of a Model-Based, Iterative Reconstruction Algorithm (MBIR) Regarding Image Quality and Dose Reduction in Liver Computed Tomography"; Investigative Radiology: vol. 48 Issue 8; Aug. 2013; pp. 598-606.

(Continued)

*Primary Examiner* — Hoon Song
(74) *Attorney, Agent, or Firm* — Thorpe North & Western, LLP

(57) ABSTRACT

A method for a practical model based computed tomography construction may include assuming that a filtered back projection reconstruction of a computed tomography image is available and acquiring a deviate of a multivariate random variable computed tomography data set. A filtered back projection reconstruction of the image may be estimated, and the filtered back projection reconstruction may be identified as a deviate of a multivariate random variable. A maximum a posteriori estimate may be generated for the filtered back projection reconstruction.

20 Claims, 12 Drawing Sheets

(56) References Cited

OTHER PUBLICATIONS

Fu et al.; "Space-Variant Channelized Preconditioner Design for 3D Iterative CT Reconstruction"; The 12$^{th}$ International Meeting on Fully Three-Dimensional Image Reconstruction in Radiology and Nuclear Medicine; 2013; pp. 205-208.

Herman et al.; "On Methods for Maximum a posteriori Image Reconstruction with a Normal Prior"; Journal of Visual Communication and Image Representation; vol. 3, No. 4; Dec. 1992; pp. 316-324.

Kim; "Accelerated Optimization Algorithms for Statistical 3D X-Ray Computed Tomography Image Reconstruction"; A dissertation submitted in partial fulfillment of the requirements for the degree of Doctor of Philosphy (Electrical Engineering: Systems; The University of Michigan; 2014; 159 pages.

Lalush et al.; "Chapter 21—Iterative Image Reconstruction"; Emission Tomography The Fundamentals of PET and SPECT; 2004; pp. 443-472.

Lange et al.; "Globally convergent algorithms for maximum a posteriori transmission tomography"; IEEE Transactions on Image Processing, vol. 4 Issue 10; Oct. 1995; pp. 1430-1438.

Nelson et al.; "New iterative reconstruction techniques for cardiovascular computed tomography: How do they work, and what are the advantages and disadvantages?"; Journal of Cardiovascular Computed Tomography, vol. 5 Issue 5; Sep.-Oct. 2011; pp. 286-292.

Sodickson; "Strategies for Reducing Radiation Exposure From Multidetector Computed Tomography in the Acute Care Setting"; Canadian Association of Radiologists Journal, vol. 64 Issue 2; May 2013; pp. 119-129.

Yadava et al.; "TU-A-201B-03: Dose Reduction and Image Quality Benefits Using Model Based Iterative Reconstruction (MBIR) Technique for Computed Tomography"; Med. Phys. 37, 3372; 2010.

Yamada et al.; "Model-based iterative reconstruction technique for ultralow-dose computed tomography of the lung: a pilot study"; Invest Radiol. Aug. 2012; vol. 47(8); pp. 482-489.

* cited by examiner

PRACTICAL MODEL BASED CT CONSTRUCTION

RELATED APPLICATION(S)

This application claims the benefit of U.S. Provisional application No. 61/865,721, filed Aug. 14, 2013.

GOVERNMENT INTEREST

None.

BACKGROUND

Renal stone disease or renal calculus disease (also known as urolithiasis) is very common, and is increasing in prevalence. Based on National Health and Nutrition Examination Survey (NHANES) data, urolithiasis impacts approximately 1 in 11 people in the United States. NHANES data also demonstrated that obese and overweight individuals have a higher prevalence of kidney stones than normal weight individuals. This disease is associated with estimated recurrence rates of 50% in the first 5-10 years after an episode of renal colic, increasing to 75% within 20 years.

Because non-contrast helical CT (computed tomography) (NCCT) is rapid, accurate, and diagnoses other pathologies that mimic renal colic, NCCT has become a standard for detection and management of this disease and the use of NCCT has risen concomitantly with the increasing incidence of urolithiasis. NCCT rapidly performs a highly sensitive and specific diagnosis of urolithiasis, with the ability to both locate calculi and often characterize the composition of the calculi.

NCCT involves exposure to ionizing radiation in order to generate diagnostic images. This exposes patients to potential risks. Estimates reflecting current use suggest that 0.7-2% of future cancers in the United States may be caused by CT-associated radiation exposures. In one estimate from 2007 data, 29,000 future cancers may be attributable to diagnostic imaging examinations. This poses a significant dilemma for the management of patients with renal stone disease, particularly because this patient population is subject to high cumulative radiation exposure. Of additional significance is that medical radiation exposure is now responsible for the majority of effective dose incurred by the US population.

The patient population impacted by urolithiasis is often young and may require repeated CT scans. This poses a significant dilemma for balancing the diagnostic benefits against the risks associated with high cumulative radiation exposure. In this context, reducing the radiation dose of the NCCT scan as much as possible becomes an important goal, but reducing dose without affecting image quality has conventionally been difficult.

A methodology that has been receiving attention recently to reduce the dose associated with a CT scan is model-based iterative reconstruction (MBIR). The MBIR methodology offers tremendous potential for dose reduction. MBIR may provide enhanced image quality with less than 1 mSv dose per exam, whereas the mean dose for an NCCT scan of the abdomen is 8.5 mSv. Such a dose reduction is enabled by accounting for the statistical distribution of noise in the CT measurements together with the usage of non-linear constraints on the image pixel values. MBIR is currently under evaluation in the clinical environment and attractive results have been reported. Unfortunately, as discussed hereafter, MBIR is currently not a practical solution due to the extensive computational effort used for its implementation.

A fundamental strength of CT is fast patient throughput. In a clinical routine, CT exams often last less than 5 minutes, and images are produced at a rate of 30 to 40 images per second. By contrast, MBIR typically involves hours of reconstruction time for a single patient, despite various applied optimizations. An affordable and robust solution for clinical routine usage of MBIR may be delayed until major advances in computing hardware are achieved as well as in the design of the MBIR methodology.

SUMMARY

Radiation dose imparted to the patient due to CT scans has become a major concern over the last few years. Model-based iterative reconstruction (MBIR) is a method that shows a lot of potential to reduce dose, but this method is computationally prohibitive. We have invented a novel iterative reconstruction scheme that retains the advantages of MBIR while being far more efficient. This approach has same dose savings as model-based iterative reconstruction, but is much less computationally extensive, so that our solution can be used for routine clinical applications of CT. The invention can also be used to reduce the dose associated with routine clinical applications of CT where maintaining workflow is important without affecting diagnostic quality.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

DETAILED DESCRIPTION

Figure 1A:
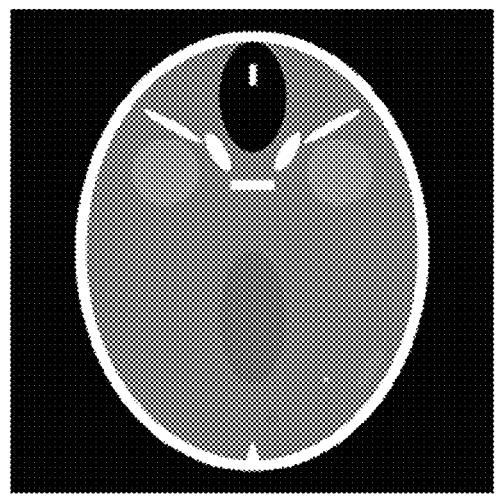
FIGS. 1A-2C illustrate results obtained of implementing Practical-MBIR using a FORBILD head phantom in accordance examples of the present technology.

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

DEFINITIONS

In describing and claiming the present invention, the following terminology will be used.

The singular forms "a," "an," and "the" include plural referents unless the context clearly dictates otherwise. Thus, for example, reference to "a particle" includes reference to one or more of such materials and reference to "subjecting" refers to one or more such steps.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Model-Based Iterative CT Construction

The following detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

As a brief overview, the present technology provides for a practical MBIR (model-based iterative reconstruction) approach that avoids computational overhead involved in conventional MBIR. Specifically, an example method may include acquiring multi-spectral x-ray tomographic data; and reconstructing a plurality of material component density images by formulating the tomographic reconstruction as a maximum a posteriori probability (MAP) estimation problem and solving the MAP estimation problem. Put differently, the method may involve acquiring a deviate of a multivariate random variable CT data set, assuming that an FBP (filtered back projection) reconstruction is available, and developing a MAP reconstruction which is based on scalar regularization (similarly as in MBIR), rather than using the FBP as an initial random starting point for iterative refining (which is typically a major source of the heavy computation time for MBIR). The modified model-based iterative reconstruction technique of the present technology avoids some of the computationally heavy maneuvers in conventional CT scanning.

The present technology is a practical model-based image reconstruction method. The method is significantly less computationally intensive than MBIR while retaining useful properties of MBIR, such as accurate noise modeling and application of non-linear constraints on the image. The present technology may be referred to as Practical-MBIR. Similarly to MBIR, the reconstructed image obtained with Practical-MBIR is the minimizer of a convex, non-linear objective function. Practical-MBIR can efficiently and accurately compute the covariance between pixels in classical filtered-backprojection (FBP) reconstructions. Mathematical (model) observers applied to computer-simulated data of an anthropomorphic phantom are usable to validate Practical-MBIR.

Computation of covariance between pixels can be a very challenging problem. Practical-MBIR provides a solution for this computation and may be applicable to other fields of imaging study other than in CT scanning environments. Practical-MBIR includes a procedure for assessing image quality, such as regarding the generation of signal present in images or regarding statistical analysis of the image quality. Practical-MBIR differs significantly from conventional solutions which are largely limited to empirical denoising methods. Similar to MBIR, Practical-MBIR is a fully model-based solution. However, unlike MBIR, Practical-MBIR is currently practical and is also applicable to all patients, including obese patients, which is particularly relevant for patients with urolithiasis. As noted previously, obese and overweight individuals have a higher prevalence of kidney stones.

Before describing further details of Practical-MBIR, an overview of MBIR will be provided for context and for understanding some similarities and some differences between Practical-MBIR and MBIR. MBIR is a model-based reconstruction algorithm that iteratively performs some algebraic computations to compare image data to a noise model. The term "iterative" refers to a computerized "guessing game" in which the algorithm predicts the correct noise and attenuation information, learns if the prediction is too high or too low, and then tries again, gradually approaching the truth and adjusting the image as a result. MBIR goes back and forth from the slice data to the raw data until coming up with an image that approximates the model. The MBIR algorithm can perform multiple iterations from multiple models. MBIR analyzes the x-ray beam from the focal spot, then analyzes the shape of the beam as it passes through the patient three-dimensionally, and again once more as the beam strikes the x-ray detector on the other side of the patient.

Let d be the vector that groups together all elements of the fanbeam CT data set (as obtained after the log operation). This vector is of length $N_\alpha N_\beta$ where $N_\alpha$ is the number of views and $N_\beta$ is the number of rays per view. Due to photon statistics as well as electronic noise, d is a multivariate random variable. To perform a model-based reconstruction, a statistical model is defined for d. In MBIR, d is viewed as a multivariate normal random variable with a diagonal covariance matrix. Hereafter, this matrix is called $C_d$. Each diagonal element of $C_d$ is the variance of one measurement. Let $\lambda$ be the number of transmitted photons, let $E(\lambda)$ be the expected value of $\lambda$, and let $\sigma_e$ be the standard deviation characterizing the electronic noise. Then, the variance of the measurement can be expressed as $\kappa^2/E(\lambda)+(\sigma_e/E(\lambda))^2$, where $\kappa$ is a constant. Whereas calibration measurements yield $\kappa$ and $\sigma_e$, $E(\lambda)$ cannot be measured. To overcome this problem, $E(\lambda)$ is replaced by or by a smoothed value of $\lambda$ obtained through a local combination of measurements. Since $E(\lambda)$ usually varies widely from one measurement to the next, the dynamic range for the diagonal elements of $C_d$ tends to be fairly large. To completely specify the statistical model for d, an expression must also be given for the expected value of d. This expression is $E(d)=A\mu$ where $\mu$ is a vector that groups together all pixel values forming the desired reconstruction, and where A is a matrix representing the forward projection model. A may be defined using a distance-driven approach. If the desired reconstruction consists of M×M pixels, then the length of $\mu$ is $M^2$, and A consists of $N_\alpha N_\beta$ rows and $M^2$ columns. A linear relationship is assumed between d and $\mu$, which implies that MBIR cannot account for non-linearities in the CT data acquisition process. Correction for these non-linearities is applied prior to reconstruction, similarly as with a conventional FBP reconstruction.

The MBIR reconstruction is formulated as a maximum a posteriori estimate (MAP) in the Bayesian framework. The mathematical expression for this estimate is $$\mu_{MBIR}=\arg\max_\mu\{P(\mu|d)\}=\arg\max_\mu\{\log P(\mu|d)\}=\arg\max_\mu\{\log P(d|\mu)+\log P(\mu)\}$$

where P(*|*) denotes a conditional probability and $P(\mu)$ is a pre-specified probability distribution for $\mu$. Given the statistical model chosen for d, this expression can be rewritten in the following more convenient form $$\mu_{MBIR}=\arg\min_\mu\{\tfrac{1}{2}(d-A\mu)^T C_d^{-1}(d-A\mu)+U(\mu)\}$$

where $U(\mu)=-\log P(\mu)$ and superscript T denotes the transpose operation. A suitable choice for $U(\mu)$ is the generalized Gaussian Markov random field with a Huber-like convex potential function.

An iterative optimization algorithm is needed to compute $\mu_{MBIR}$. The algorithm used may be the coordinate descent method or other suitable algorithm, such as based on surrogate functions or augmented Lagrangian. Because the diagonal elements of $C_d$ cover a wide dynamic range, fast convergence for the computation of $\mu_{MBIR}$ is challenging. To alleviate this difficulty, a classical FBP reconstruction is used to start the iterative optimization process of MBIR. Although $\mu_{MBIR}$ is uniquely defined, this initial guess can significantly impact the reconstruction because only a finite number of iterations can be used in practice and the asymptotic convergence rate of iterative reconstruction algorithms is typically very low.

As an item of note, a different value has to be used for M when using MBIR for reconstruction instead of an FBP method. Using the latter, a region-of-interest (ROI) can be selected up front and reconstruction can be performed over this region only. For this reason, most CT scanners only offer M=512 and let the technologist determine the ROI over which the pixels have to be distributed. This region can be as large as the field-of-view (FOV) diameter, i.e., 50 cm, and as small as 5 cm, and the pixel size can thus vary from 0.01 cm to 0.1 cm. MBIR does not offer this property. MBIR requires the pixels to cover the entire FOV and even more when the patient is obese. Therefore, for a non-obese patient, M must be as large as 1024 for a pixel size of 0.05 cm, and as large as 2048 for a pixel size of 0.025 cm. For an obese patient that fills the 70 cm gantry opening of a CT scanner, the numbers of M become as large as 1433 and 2866 for pixels size of 0.05 cm and 0.025 cm, respectively. This is one of the reasons why an efficient implementation of MBIR is challenging. Aside from requiring a larger M value, applying MBIR to patients that extend beyond the FOV poses major difficulties since MBIR attempts to perform accurate reconstruction both inside and outside the FOV, whereas reconstruction outside the FOV is a highly ill-posed problem. Thus, MBIR may never be suitable for obese patients.

Also, A is usually very large, so that direct storage of A is not practical. In two dimensions where M=1024, $N_\alpha$=672, $N_\beta$=2×1160 (to account for a flying focal spot), A includes approximately 3.5 billion non-zero elements, which requires about 13 GB of memory in a 32-bit floating-point representation (assuming 2.2×1024 pixels participate in each measurement, which is a reasonable estimate for the distance-driven approach). For three dimensions, the amount of data to be stored increases significantly.

Turning now to Practical-MBIR, Practical-MBIR is a statistics-driven solution that is formulated, similarly to MBIR, as a maximum a posteriori (MAP) estimate in the Bayesian framework. As with MBIR, a method may start by acknowledging that the CT data set is a deviate of a multivariate random variable. An assumption may be made that a classical FBP reconstruction is available. Next, however, the method departs from MBIR. Instead of viewing the FBP reconstruction as the initial guess for an iterative optimization procedure, an observation may be made that, being a function of the CT data, the FBP reconstruction is itself a deviate of a multivariate random variable. In the context of the adopted Bayesian framework, this observation leads to the following MAP estimate $$\hat{\mu}=\arg\max_\mu\{P(\mu|\mu_{FBP})\}=\arg\max_\mu\{\log P(\mu|\mu_{FBP})\}=\arg\max_\mu\{\log P(\mu_{FBP}|\mu)+\log P(\mu)\}$$

where $\mu_{FBP}$ is the FBP reconstruction, and log $P(\mu)$ is the same scalar regularization term as in MBIR. The MAP estimate introduced here may represent the Practical-MBIR solution. To move forward from the estimate a statistical model for the CT data may be introduced, similarly as with MBIR, so that the conditional probability for $\mu_{FBP}$ may be specified. The same statistical model as in MBIR may be used. Under this assumption, $\mu_{FBP}$ is a deviate of a multivariate normal random variable. Therefore, the Practical-MBIR solution can be rewritten in the form $$\hat{\mu} = \arg\min_\mu \{½(\mu-\mu_{FBP})^T C^{-1} (\mu-\mu_{FBP}) + U(\mu)\}$$

where C is the covariance matrix for $\mu_{FBP}$.

In computing this expression of $\hat{\mu}$, some observations can be made. The solution is well-defined for any strength. In particular, when $U(\mu)=0$, which would be acceptable for low-noise data, the Practical-MBIR solution reduces to $\mu_{FBP}$, whereas the MBIR solution becomes unstable (due to mismatch between the data and the forward projection model as much as noise). Also, Practical-MBIR preserves the attractive ROI feature of FBP. That is, with Practical-MBIR, M=512 may be used with discretion given to the technologist to determine the region over which the pixels have to be distributed, exactly as in current CT scanners. Further, because Practical-MBIR preserves the attractive ROI feature of FBP, and because satisfactory data truncation handling methods exist for FBP, Practical-MBIR is well-suited for all patients, including obese patients.

It is noted that Practical-MBIR can either be implemented on a global scale, as described above, or using partitions. In other words, the ROI may be divided into sub-regions, and the Practical-MBIR method may be applied over each sub-region, and then the sub-regions may be recombined together. Applying Practical-MBIR to sub-regions in this manner can result in Practical-MBIR being an even more efficient solution compared with MBIR than it may already be when using the global approach. Merging sub-regions together may normally introduce boundary artefacts. However, seamless merging can be achieved because the correlation between any two pixels in $\mu_{FBP}$ decreases quickly with the distance between the pixels. Thus, some overlap between the subregions may be provided, using an overlap length that is commensurate with the distance beyond which correlations between pixels can be neglected. To further reduce potential boundary artefacts, only the central part of each sub-region may be used for the merging operation.

Note that C is not diagonal, and that C is fairly large (with a size of $M^2 \times M^2$), although not as large as A because M=512 may be used in Practical-MBIR. Therefore, the development of Practical-MBIR presents many challenges such as how to compute C efficiently and accurately, storage of C, computation of $C^{-1}$, and so forth. These issues are addressed in the following discussion. Also, it is noted that the solutions to these issues are scalable to 3D (three dimensional) multi-slice CT.

At first glance, it may appear as though A plays no role in Practical-MBIR. However, this is misleading because a backprojection algorithm is used to compute $\mu_{FBP}$. This backprojection can be implemented in many ways, including using $A^T$. To keep Practical-MBIR as close to MBIR as possible, FBP may be implemented using $A^T$ for the backprojection step, with A being the forward-projection matrix used in MBIR, i.e., the distance-driven approach. The present covariance computation method, described hereafter, can be adjusted accordingly.

Given that the FBP algorithm is linear, it is not difficult to obtain an expression for C. Due to the linearity, there exists a matrix R such that $\mu_F = Rd$, which yields $C = RC_d R^T$. Unfortunately, direct use of this expression is not practical since $O(N_\alpha N_\beta M^2)$ operations are needed to obtain R. Moreover computing the matrix product requires $O(N_\alpha N_\beta M^4)$ operations, where $O(*)$ means "on the order of". A much more efficient method may be used. The method may be based on an assumption that correlations between pixels in an FBP reconstruction are of short range, i.e., a pixel is only significantly correlated with a small number of other pixels, called $m^2$, where m is an odd number. This assumption will be substantiated below. Also, the method may be based on findings that the convolution-backprojection structure of the FBP algorithm can be transferred to the computation of C. In other words, C can be computed as the backprojection of pre-filtered data consisting of the non-zero elements of $C_d$, which effectively reduces the number of operations by $N_\beta$. Combining the assumption and findings together brings the number of operations down to $O(N_\alpha M^2 m^2)$, which is entirely acceptable and practical, especially if m is small. Generally, using a value of m that is less than or equal to 7 is sufficient. Computational costs will be discussed further after other aspects are described.

Most CT manufacturers rebin the data into a parallel-beam (PB) geometry (wedge geometry in 3D), make use of a flying focal spot, and sometimes even interleave data separated by 180 degrees. Practical-MBIR is able to accommodate these various features. The accuracy of the present covariance computation method in these CT scanners will be described with reference to FIGS. 1A-2C. The results in FIGS. 1A-2C were obtained using a FORBILD head phantom, which is widely employed by CT scientists. The phantom may be defined by simple geometric objects such as spheres, cylinders, ellipsoids or cones. The phantom may provide a simple representation of anatomical structures which are useful in evaluating CT image quality.

Figure 1B:
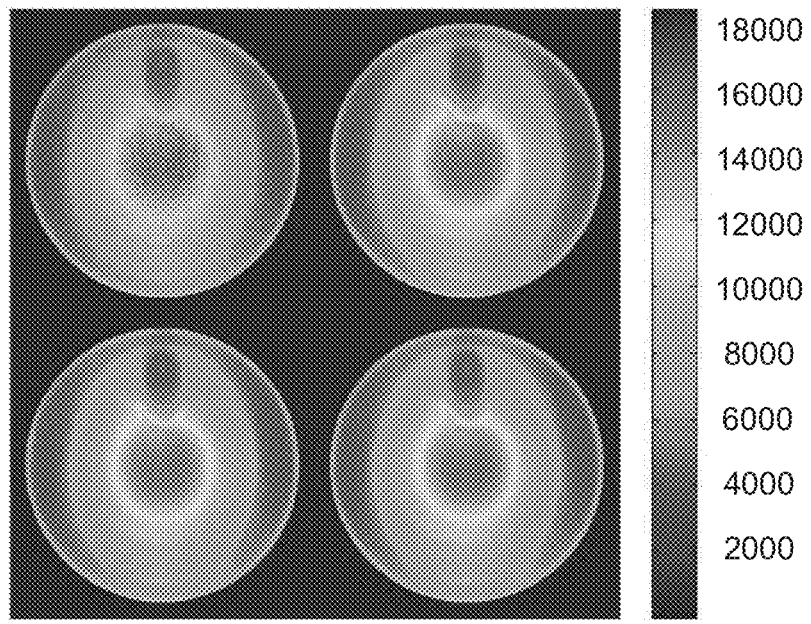
Figure 1C:
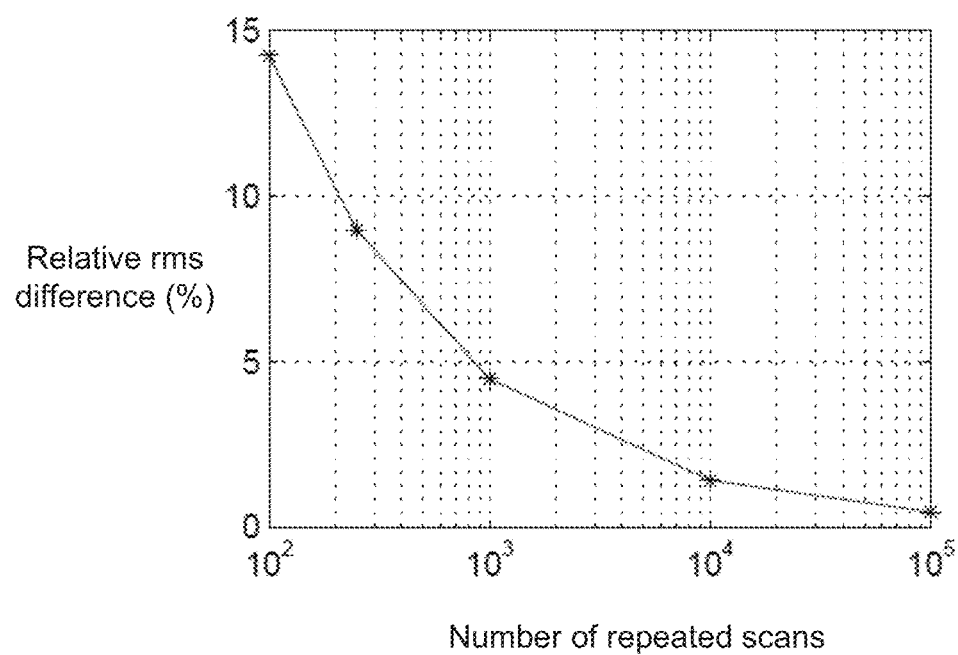

Fanbeam CT data were simulated on a short-scan with flying focal spot, and reconstruction was performed using parallel-beam rebinning with an upsampling factor of 2 in each view. To evaluate the ability to predict the noise properties of the reconstruction, which are summarized in C, 105 fanbeam data sets with Poisson noise were created. Reconstruction from each of these sets was performed and the sample variance and covariance was used to obtain benchmarking estimates of these properties. The noise addition was based on a model that includes a water-cylinder-compensating bowtie filter and tube current modulation. The scanning parameters were representative of a clinical CT scanner with a detector size equal to 0.075 cm at FOV center, and reconstruction was performed with a pixel size of 0.05 cm. FIGS. 1A-1C illustrate pixel variance computation. FIG. 1A illustrates a FORBILD head phantom used to test accuracy of variance and covariance images given by Practical-MBIR. FIG. 1B illustrates variance images (in $HU^2$) obtained from $10^2$, $10^3$ and $10^4$ noise realizations (top left, top right, bottom left, respectively), and using Practical-MBIR (bottom right). FIG. 1C illustrates a relative root mean square difference, in percentages, between Practical-MBIR and the sample variance. In a variance image, each pixel value is the variance of the pixel located at the same place within the reconstruction. A variance image is a convenient way to display the elements lying on the diagonal of C. The sample variance estimate based on $10^5$ noise realizations differs from the Practical-MBIR result by only 0.45%.

Figure 2A:
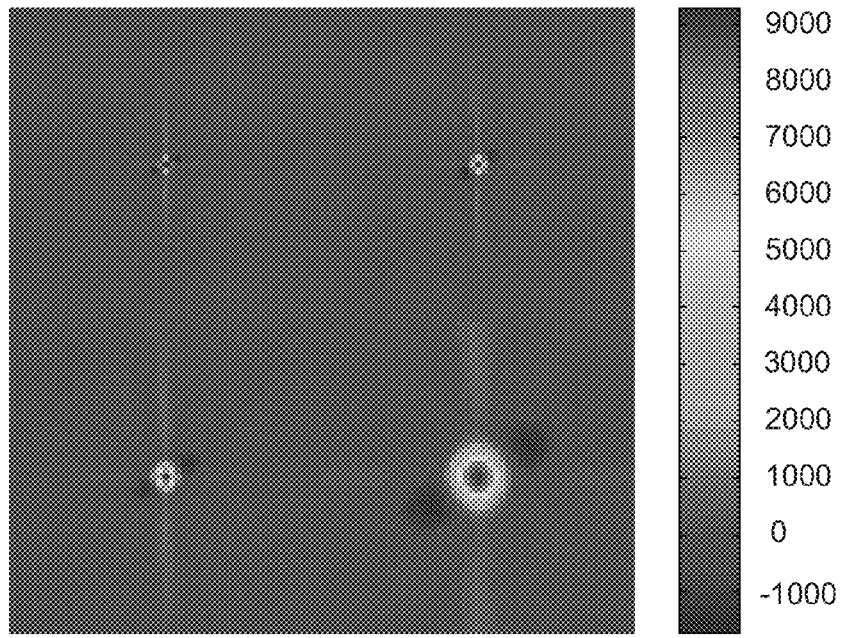
Figure 2B:
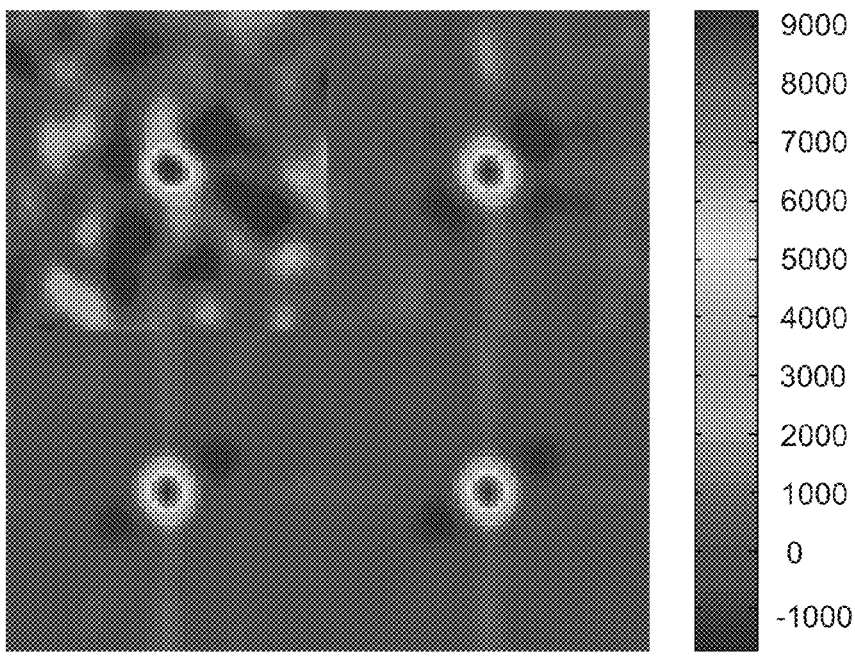
Figure 2C:
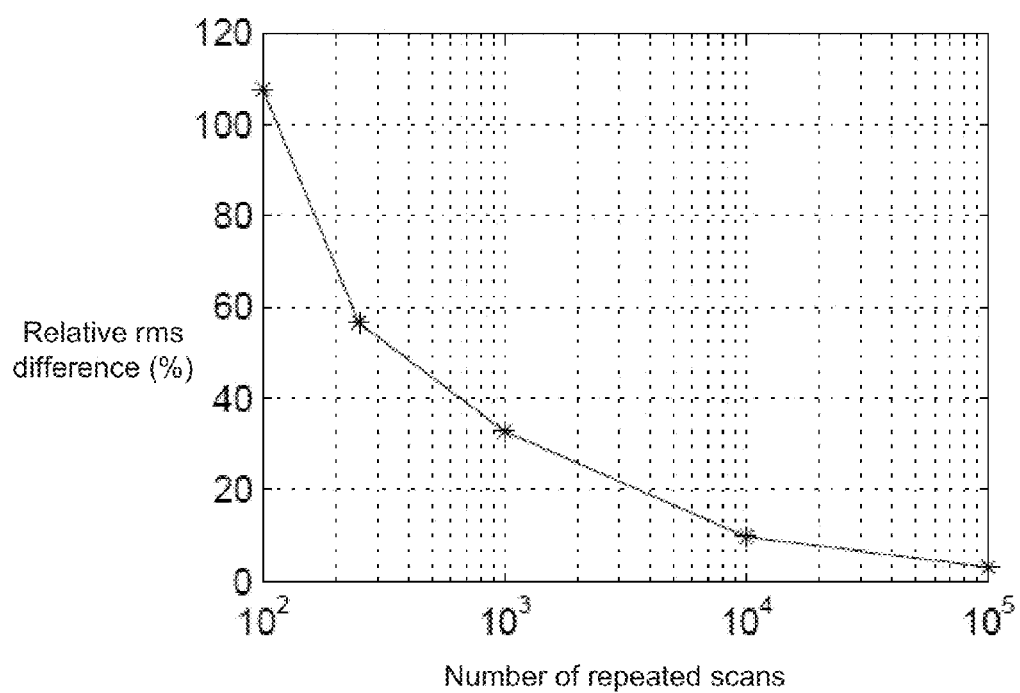

FIG. 2A depicts analytical covariance images for the reference pixel shown as the white dot in FIG. 1A, as obtained when the pixel size used for reconstruction is 0.05 cm (top left), 0.036 cm (top right), 0.023 (bottom left), and 0.01 cm (bottom right). FIG. 2B illustrates covariance images (in $HU^2$ and for the pixel size of 0.01 cm) obtained with 100, 1000 and 10000 noise realizations (top left, top right, and bottom left, respectively), and the Practical-MBIR method (bottom right). FIG. 2C illustrates the relative root mean square difference, in percentages.

A covariance image is a convenient way of displaying a row (or portion of) a row of C. A covariance image displays the covariance between a reference pixel and the pixels that surround the reference pixel. The central pixel value in a covariance image is thus equal to the variance of the reference pixel. The reference pixel that was selected here is identified by the white dot in FIG. 1A. The comparison of covariance images in FIG. 2B shows that a pixel is only significantly correlated with a small number, $m^2$, of surrounding pixels, and m decreases as the pixel size increases. Because the covariance image with pixel size of 0.01 cm exhibits more structure, the Practical-MBIR was validated using the pixel size of 0.01 mm (see FIGS. 2B and 2C). The sample covariance estimate based on $10^5$ noise realizations differs from our results by only 3.03%.

The results presented thus far for computation of C assumed that the variance of the CT data is exactly known, which is not realistic. Practical-MBIR may thus use a covariance computation method that relies only on the patient CT scan. This is analogous to MBIR where statistical weights have to be estimated because $E(\lambda)$ is not available. The same approach as in MBIR may be used. In other words, the variance of each measurement may be estimated by $\kappa^2/\lambda+(\sigma_e/\lambda)^2$ or a smoothed version of this estimate. This approach was validated using computer simulated data, as shown in FIGS. 3A-3E.

Figure 3A:
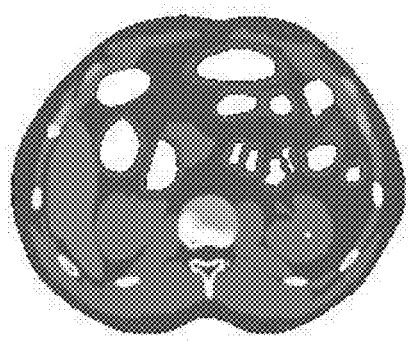
FIGS. 3A-3E illustrate variance and covariance computation from a single noisy CT scan with a pixel size of 0.05 cm in accordance examples of the present technology.
Figure 3B:
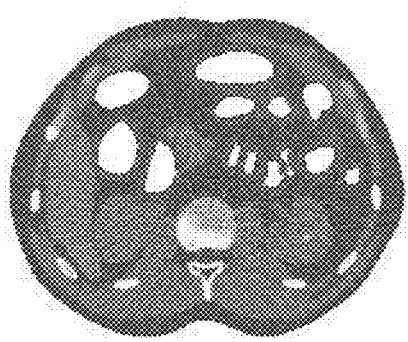
Figure 3C:
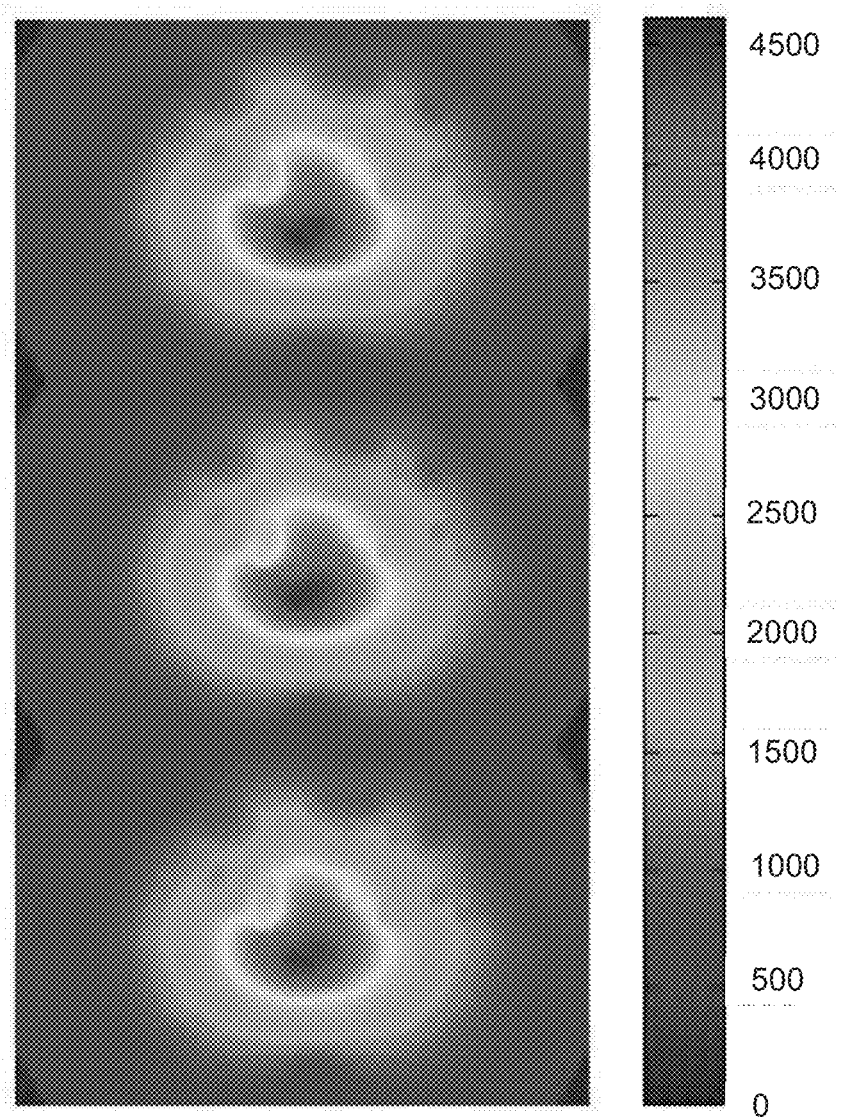
Figure 3D:
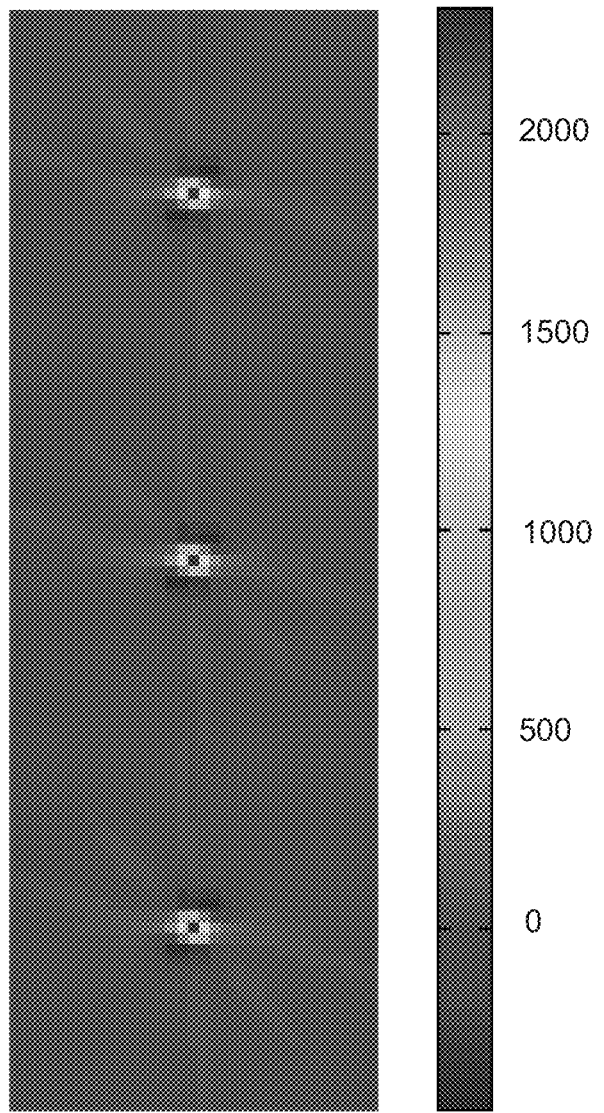
Figure 3E:
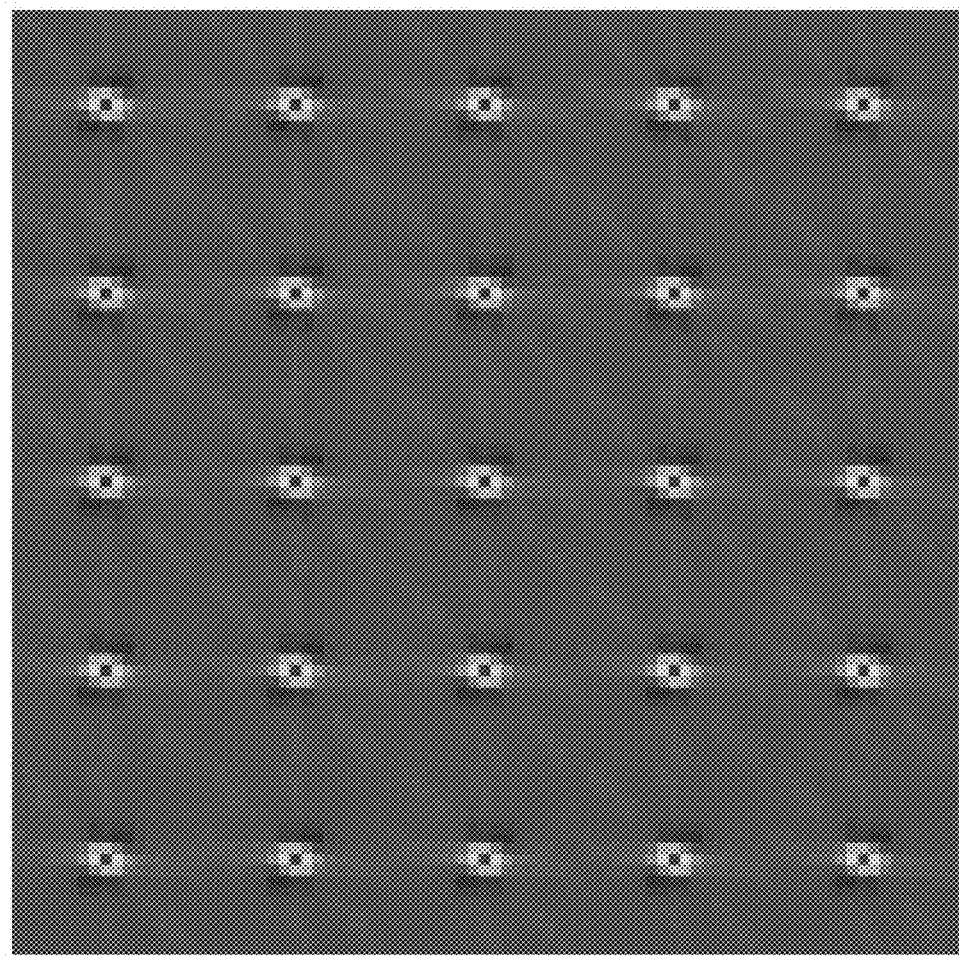

FIGS. 3A-3E illustrate variance and covariance computation from a single noisy CT scan (smooth bowtie filter, tube current modulation), with a pixel size of 0.05 cm. FIG. 3A illustrates an XCAT phantom with a stone in one kidney. FIG. 3B illustrates a reconstruction from the noisy scan. FIG. 3C illustrates an exact variance image for the phantom without the kidney stone (top) and with the kidney stone (middle). FIG. 3C further includes a variance image estimated from the noisy CT scan with the stone present (bottom). FIG. 3D includes covariance images arranged in the same way, using the kidney stone location as a reference pixel. FIG. 3E includes exact covariance images obtained when the reference pixel is moved around by 1 or 2 pixels.

A relative root mean square difference of less than 1.05% was observed for both variance and covariance computation. Two additional effects were also tested, including (i) the impact of the presence/absence of a stone (3 mm, 600 HU), and (ii) spatial dependence of the covariance image. The first test showed that the impact of the stone presence on variance/covariance was less than 5%. The second test showed that covariance images vary slowly with the position of the reference pixel. Based on this, computation of C may be further sped up. Rather than computing all rows of C, only a fraction of these rows can be computed using reference pixels that correspond to a downsampled version of the reconstruction, and interpolation will yield the other rows. In addition to downsampling, a coarser discretization of the analytical integral $\alpha$ (the view angle), which is approximated by the formula underlying the efficient variance/covariance computation, can yield comparable results with an increase in speed by a factor of 2 to 3 by further reducing computational effort.

Given the foregoing, the number of operations to compute C is $O((N_\alpha/2)(Mm/q)^2)$ in 2D and $O((N_\alpha/2)M^2N(m/q)^3)$ in 3D where q is the downsampling factor and N is the number of slices. For m=7 and q=4, this cost is about that of 4 FBP reconstructions, which is far from being prohibitive, especially since M=512. Moreover, unlike in MBIR, all operations are in the parallel-beam (PB) (wedge) geometry, which provides another acceleration factor of about 4 over the computation of $A\mu$. In some instances, using q=4 be too much downsampling in the axial direction for a large slice thickness, but then m=7 would also be too large, so that $m/q \cong 2$ is reasonable. Since computation of C may involve the equivalent computation of 4 FBP reconstructions, storing C in memory is contemplated. In 2D, the size of C is insignificant. In 3D, $(M/q)^2(N/q)m^3$ 4-byte floating-point numbers are used to store C. Thus, in 3D, for M=512, N=300, m=7 and q=4, only 1.6 gigabytes of storage or memory is used, which is practical. This number can be further reduced by using a small amount of partitioning across slices.

Regarding the issue of $C^{-1}$ mentioned previously, computing $C^{-1}$ may seem prohibitive. However, this can be overcome with a change of variables. Using $\mu=Cx$, it is observed that $\hat{\mu}=C\hat{x}$ with $$\hat{x}=\arg\min_x\{\tfrac{1}{2}x^T Cx - \mu_F^T x + U(Cx)\}$$

which is much easier to solve since $C^{-1}$ is not needed anymore. To compute $\hat{x}$, the iterative coordinate descent method in MBIR may be used. Because the correlation between pixels are short range, high parallelization is possible. In other words, many elements of x can be updated independently, so that the effort for computation of $\hat{x}$ is not much of a concern.

Figure 4:
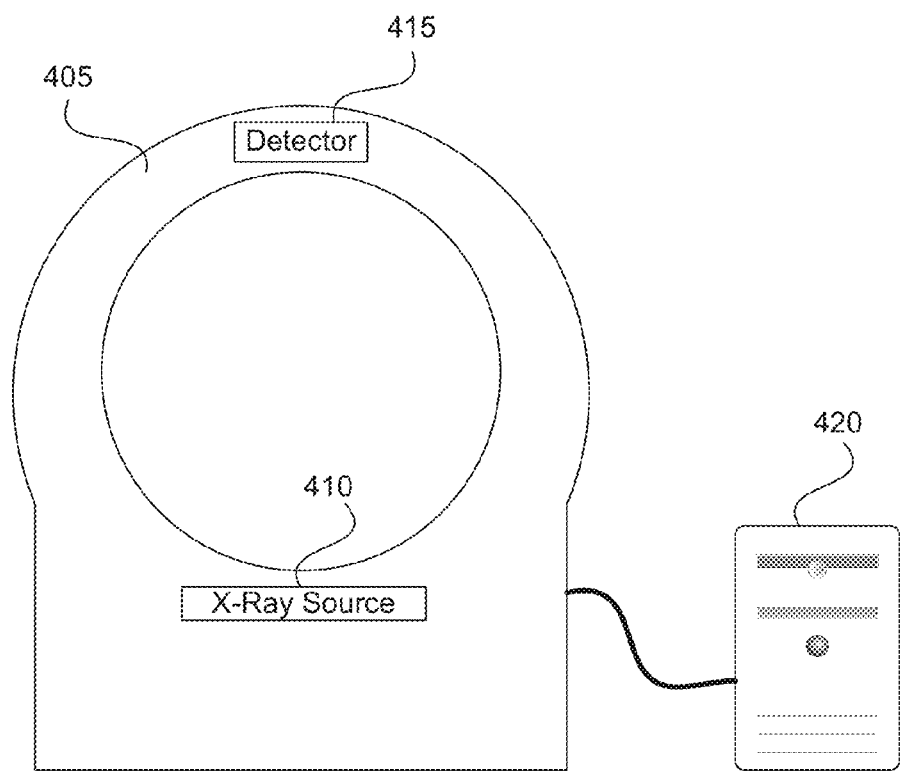
FIG. 4 is a block diagram of a computed tomography system for implementing Practical-MBIR in accordance with an example of the present technology.

Referring to FIG. 4, a simplistic block diagram of a tomographic imaging system is illustrated in accordance with an example of the present technology. The system may include an x-ray source 410 configured to generate a beam of radiation. The system may further include a detector 415 or detector array configured to receive the beam of radiation. The x-ray source 410 and the detector 415 may be contained within a gantry of a CT device 405. An image reconstructor 420 may be a part of the CT device or may be a computing device in communication with the CT device. For example, the image reconstructor 420 may be in communication with the X-ray source and the detector array for receiving image data.

The image reconstructor 420 may be configured to estimate a filtered back projection reconstruction of the image; specify a statistical model for a conditional probability of the filtered back projection reconstruction of the image; and calculate a reconstruction of the image based on the estimated filtered back projection reconstruction and the conditional probability. The image reconstructor 420 may be further configured to calculate a covariance matrix for the filtered back projection reconstruction as a backprojection of pre-filtered data consisting of the non-zero elements of a diagonal covariance matrix.

The image reconstructor 420 may be a computing device or may be implemented on a computing device, the computing device including a processor and a memory. The memory may be a memory device. The memory device may be configured for storing the covariance matrix. A capacity of the memory device may vary between applications. However, in one example, storing the covariance matrix may use less than 2 gigabytes of capacity of the memory device. The image reconstructor 420 may be further configured to compute the covariance matrix for three dimensions at a computational cost corresponding to approximately four filtered back projection reconstructions. In other words, the covariance matrix may be computed at a fraction of the computing cost of conventional MBIR.

In one example, the image reconstructor 420 may be configured to identify a short range of correlations between pixels in the reconstruction. The number of pixels within the short range is $m^2$. m may be an odd number less than or equal to 5 or 7 or 9, for example. The image reconstructor may be further configured to set a downsampling factor of the reconstruction that is whole number approximately half the value of m.

Figure 5:
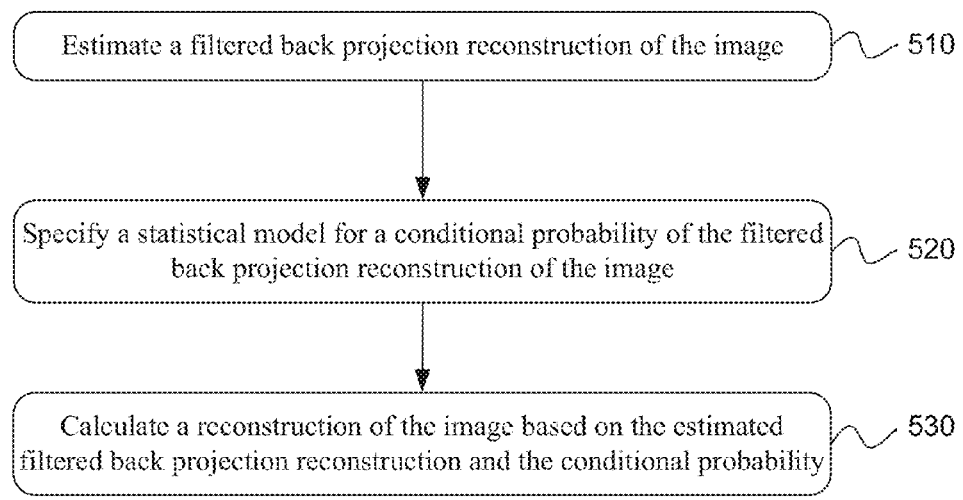
FIGS. 5-6 are flow diagrams for methods of implementing Practical-MBIR in accordance with examples of the present technology.
Figure 6:
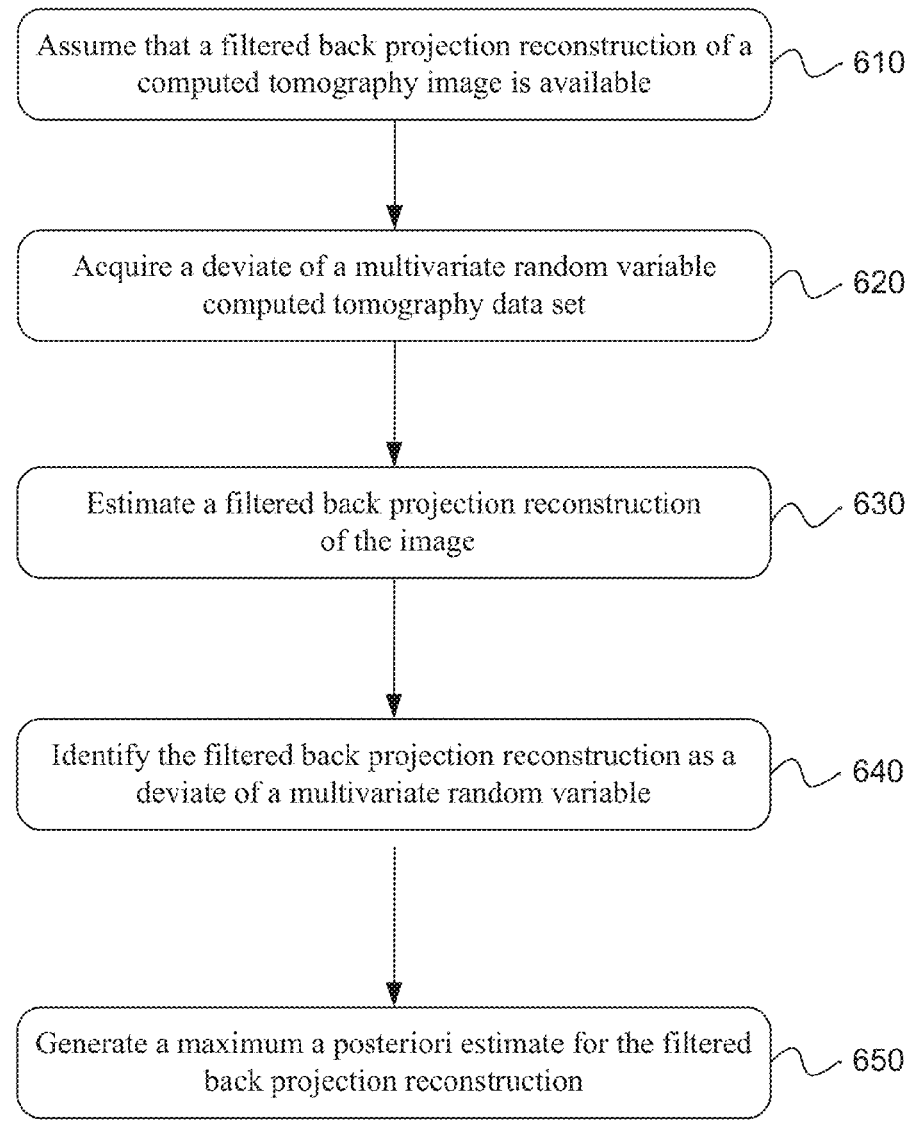

FIGS. 5-6 illustrate flow diagrams of methods according to the present technology. For simplicity of explanation, the methods are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events. Additionally, it should be appreciated that the methods disclosed in this specification are capable of being stored on an article of manufacture to facilitate transporting and transferring such methods to computing devices. The term article of manufacture, as used herein, is intended to encompass a computer program accessible from any computer-readable device or storage media.

Additional example details, operations, options, variations, etc. that may be part of the method have been described previously herein and/or are described in further detail below. Various systems, devices, components, modules and so forth for implementing the method may also be used, as described with respect to the various examples included in this disclosure.

Referring now to FIG. 5, a flow diagram of a method is illustrated in accordance with an example of the present technology. The method may include being implemented on a computing device. The computing device may include a processor, a memory in electronic communication with the processor, and instructions stored in the memory. The instructions may be executable by the processor to perform the method of FIG. 5.

The method may include estimating 510 a filtered back projection reconstruction of the image. The method may further include specifying 520 a statistical model for a conditional probability of the filtered back projection reconstruction of the image. A reconstruction of the image may be calculated 530 based on the estimated filtered back projection reconstruction and the conditional probability. The method may further include performing the estimating, specifying and calculating across an entire region of interest of the image. In an alternative example, the method may include dividing a region of interest of the image into sub-regions and estimating, specifying and calculating across each of the sub-regions separately. After estimating, specifying and calculating across each of the sub-regions, the method may include combining the sub-regions together. When dividing the region of interest into the sub-regions, the sub-regions may be divided to include a region of overlap with adjacent sub-regions.

The method may include calculating a maximum a posteriori estimate in a Bayesian framework using the formula $$\hat{\mu}=\arg\max_\mu\{P(\mu|\mu_{FBP})\}=\arg\max_\mu\{\log P(\mu|\mu_{FBP})\}=\arg\max_\mu\{\log P(\mu_{FBP}|\mu)+\log P(\mu)\}$$

where $\hat{\mu}$ is the reconstruction, $\mu$ is a vector for grouping pixel values forming the reconstruction, $\mu_{FBP}$ is the estimated filtered back projection reconstruction, and log $P(\mu)$ is a scalar regularization term. The method may still further include specifying a conditional probability for $\mu_{FBP}$, where $\mu_{FBP}$ is a deviate of a multivariate normal random variable, the formula is rewritten as $$\hat{\mu}=\arg\min_\mu\{\tfrac{1}{2}(\mu-\mu_{FBP})^T C^{-1}(\mu-\mu_{FBP})+U(\mu)\}$$

where C is a covariance matrix for $\mu_{FBP}$, $U(\mu)$ is a Guassian Markov random field with a Huber-like convex potential function, and T represents a transpose operation. In one example, the covariance matrix may be calculated by computing a subset of rows of the covariance matrix using reference pixels that correspond to a downsampled version of the reconstruction, and interpolating a remainder of the rows.

The method may include defining a number of pixels in the reconstruction in one dimension as 512, for example. The method may also include receiving input specifying selection of a region of interest over which the pixels are to be distributed.

Referring now to FIG. 6, a flow diagram of another method is illustrated in accordance with an example of the present technology. The method may be a computer-implemented method. The method may include assuming 610 that a filtered back projection reconstruction of a computed tomography image is available and acquiring 620 a deviate of a multivariate random variable computed tomography data set. A filtered back projection reconstruction of the image may be estimated 630, and the filtered back projection reconstruction may be identified 640 as a deviate of a multivariate random variable. A maximum a posteriori estimate may be generated 650 for the filtered back projection reconstruction.

In a further example, the method may include estimating the filtered back projection reconstruction for subjects that extend beyond a field of view for a computed tomography device used to acquire the computed tomography image. Thus, the method may be applied to obese or overweight individuals.

Similarly as mentioned in the description of the method illustrated in FIG. 5, additional example details, operations, options, variations, etc. that may be part of the method illustrated in FIG. 6 have been described previously herein and/or are described in further detail below. Various systems, devices, components, modules and so forth for implementing the method may also be used, as described with respect to the various examples included in this disclosure.

Figure 7:
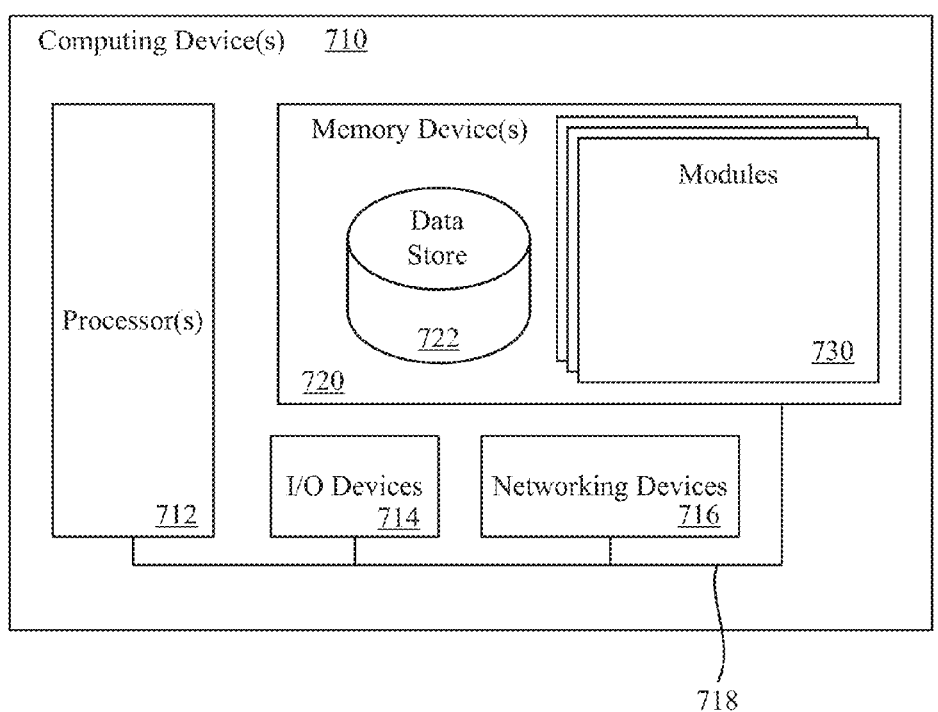
FIG. 7 is a block diagram of a computing system for implementing Practical-MBIR in accordance with an example of the present technology

FIG. 7 illustrates a computing device 710 on which services or modules of this technology may execute. A computing device 710 is illustrated on which a high level example of the technology may be executed. The computing device 710 may include one or more processors 712 that are in communication with memory devices 720. The computing device 710 may include a local communication interface 718 for the components in the computing device. For example, the local communication interface 718 may be a local data bus and/or any related address or control busses as may be desired.

The memory device 720 may contain modules 730 that are executable by the processor(s) and data for the modules. A data store 722 may also be located in the memory device 720 for storing data related to the modules and other applications along with an operating system that is executable by the processor(s) 712.

Various applications may be stored in the memory device 720 and may be executable by the processor(s) 712. Components or modules discussed in this description that may be implemented in the form of software using high programming level languages that are compiled, interpreted or executed using a hybrid of the methods.

The computing device 710 may also have access to I/O (input/output) devices 714 that are usable by the computing devices. An example of an I/O device 714 is a display screen that is available to display output from the computing devices. Other known I/O device may be used with the computing device as desired. Networking devices 716 and similar communication devices may be included in the computing device 710. The networking devices 716 may be wired or wireless networking devices 716 that connect to the internet, a LAN, WAN, or other computing network.

The components or modules that are shown as being stored in the memory device 720 may be executed by the processor 712. The term "executable" may mean a program file that is in a form that may be executed by a processor 712. For example, a program in a higher level language may be compiled into machine code in a format that may be loaded into a random access portion of the memory device 720 and executed by the processor 712, or source code may be loaded by another executable program and interpreted to generate instructions in a random access portion of the memory to be executed by a processor 712. The executable program may be stored in any portion or component of the memory device 720. For example, the memory device 720 may be random access memory (RAM), read only memory (ROM), flash memory, a solid state drive, memory card, a hard drive, optical disk, floppy disk, magnetic tape, or any other memory components.

The processor 712 may represent multiple processors and the memory 720 may represent multiple memory units that operate in parallel to the processing circuits. This may provide parallel processing channels for the processes and data in the system. The local interface may be used as a network to facilitate communication between any of the multiple processors and multiple memories. The local interface may use additional systems designed for coordinating communication such as load balancing, bulk data transfer, and similar systems.

While the flowcharts presented for this technology may imply a specific order of execution, the order of execution may differ from what is illustrated. For example, the order of two more blocks may be rearranged relative to the order shown. Further, two or more blocks shown in succession may be executed in parallel or with partial parallelization. In some configurations, one or more blocks shown in the flow chart may be omitted or skipped. Any number of counters, state variables, warning semaphores, or messages might be added to the logical flow for purposes of enhanced utility, accounting, performance, measurement, troubleshooting or for similar reasons.

Some of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more blocks of computer instructions, which may be organized as an object, procedure, or function. Nevertheless, the executables of an identified module need not be physically located together, but may comprise disparate instructions stored in different locations which comprise the module and achieve the stated purpose for the module when joined logically together.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices. The modules may be passive or active, including agents operable to perform desired functions.

The technology described here may also be stored on a computer readable storage medium that includes volatile and non-volatile, removable and non-removable media implemented with any technology for the storage of information such as computer readable instructions, data structures, program modules, or other data. Computer readable storage media include, but is not limited to, RAM, ROM, EEPROM, flash memory or other memory technology, CD-ROM, digital versatile disks (DVD) or other optical storage, magnetic cassettes, magnetic tapes, magnetic disk storage or other magnetic storage devices, or any other computer storage medium which may be used to store the desired information and described technology. The computer readable storage medium may, for example, be in the form of a non-transitory computer readable storage medium. As used herein, the terms "medium" and "media" may be interchangeable with no intended distinction of singular or plural application unless otherwise explicitly stated. Thus, the terms "medium" and "media" may each connote singular and plural application.

The devices described herein may also contain communication connections or networking apparatus and networking connections that allow the devices to communicate with other devices. Communication connections are an example of communication media. Communication media typically embodies computer readable instructions, data structures, program modules and other data in a modulated data signal such as a carrier wave or other transport mechanism and includes any information delivery media. A "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared, and other wireless media. The term computer readable media as used herein includes communication media.

It is noted that any of the distributed system implementations described above, or any of their components, may be implemented as one or more web services. In some implementations, a web service may be implemented by a software and/or hardware system designed to support interoperable machine-to-machine interaction over a network. A web service may have an interface described in a machine-processable format, such as the Web Services Description Language (WSDL). Other systems may interact with the web service in a manner prescribed by the description of the web service's interface. For example, the web service may define various operations that other systems may invoke, and may define a particular application programming interface (API) to which other systems may be expected to conform when requesting the various operations.

Reference was made to the examples illustrated in the drawings, and specific language was used herein to describe the same. It will nevertheless be understood that no limitation of the scope of the technology is thereby intended. Alterations and further modifications of the features illustrated herein, and additional applications of the examples as illustrated herein, which would occur to one skilled in the relevant art and having possession of this disclosure, are to be considered within the scope of the description.

Furthermore, the described features, structures, or characteristics may be combined in any suitable manner in one or more examples. In the preceding description, numerous specific details were provided, such as examples of various configurations to provide a thorough understanding of examples of the described technology. One skilled in the relevant art will recognize, however, that the technology may be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements may be devised without departing from the spirit and scope of the described technology.

The invention claimed is:

1. A computing device that is configured to reconstruct an image from a tomographic imaging system, comprising:
   a processor;
   a memory in electronic communication with the processor;
   instructions stored in the memory, the instructions being executable by the processor to perform a method, comprising:
   estimating a filtered back projection reconstruction of the image;
   specifying a statistical model for a conditional probability of the filtered back projection reconstruction of the image; and
   calculating a reconstruction of the image based on the estimated filtered back projection reconstruction and the conditional probability.

2. The device of claim 1, wherein the method further comprises estimating, specifying and calculating across an entire region of interest of the image.

3. The device of claim 1, wherein the method further comprises dividing a region of interest of the image into sub-regions and estimating, specifying and calculating across each of the sub-regions separately.

4. The device of claim 3, wherein the method further comprises combining the sub-regions together after estimating, specifying and calculating across each of the sub-regions.

5. The device of claim 3, wherein the method further comprises dividing the sub-regions to include a region of overlap with adjacent sub-regions.

6. The device of claim 1, wherein the method further comprises calculating a maximum a posteriori estimate in a Bayesian framework using the formula $$\hat{\mu} = \arg\max_\mu \{P(\mu|\mu_{FBP})\} = \arg\max_\mu \{\log P(\mu|\mu_{FBP})\} = \arg\max_\mu \{\log P(\mu_{FBP}|\mu) + \log P(\mu)\}$$

where $\hat{\mu}$ is the reconstruction, $\mu$ is a vector for grouping pixel values forming the reconstruction, $\mu_{FBP}$ is the estimated filtered back projection reconstruction, and $\log P(\mu)$ is a scalar regularization term.

7. The device of claim 6, wherein the method further comprises specifying a conditional probability for $\mu_{FBP}$, where $\mu_{FBP}$ is a deviate of a multivariate normal random variable, the formula is rewritten as $$\hat{\mu} = \arg\min_\mu \{\tfrac{1}{2}(\mu - \mu_{FBP})^T C^{-1}(\mu - \mu_{FBP}) + U(\mu)\}$$

where C is a covariance matrix for $\mu_{FBP}$, $U(\mu)$ is a Guassian Markov random field with a Huber-like convex potential function, and T represents a transpose operation.

8. The device of claim 7, wherein the method further comprises calculating the covariance matrix by computing a subset of rows of the covariance matrix using reference pixels that correspond to a downsampled version of the reconstruction, and interpolating a remainder of the rows.

9. The device of claim 1, wherein the method further comprises defining a number of pixels in the reconstruction in one dimension as 512.

10. The device of claim 9, wherein the method further comprises receiving input specifying selection of a region of interest over which the pixels are to be distributed.

11. A tomographic imaging system comprising:
    an x-ray source configured to generate a beam of radiation;
    a detector array configured to receive the beam of radiation; and
    an image reconstructor in communication with the X-ray source and the detector array for receiving image data, the image reconstructor configured to:
    estimate a filtered back projection reconstruction of the image;
    specify a statistical model for a conditional probability of the filtered back projection reconstruction of the image; and
    calculate a reconstruction of the image based on the estimated filtered back projection reconstruction and the conditional probability.

12. The system of claim 11, wherein the image reconstructor is further configured to calculate a covariance matrix for the filtered back projection reconstruction as a backprojection of pre-filtered data consisting of the non-zero elements of a diagonal covariance matrix.

13. The system of claim 12, further comprising a memory device for storing the covariance matrix.

14. The system of claim 13, wherein storing the covariance matrix uses less than 2 gigabytes of capacity of the memory device.

15. The system of claim 12, wherein the image reconstructor is further configured to compute the covariance matrix for three dimensions at a computational cost corresponding to approximately four filtered back projection reconstructions.

16. The system of claim 11, wherein the image reconstructor is further configured to identify a short range of correlations between pixels in the reconstruction, wherein the number of pixels within the short range is $m^2$, where m is an odd number less than or equal to 7.

17. The system of claim 16, wherein the image reconstructor is further configured to set a downsampling factor of the reconstruction that is approximately half the value of m.

18. A non-transitory computer-readable medium comprising computer-executable instructions which, when executed by a processor, implement a method, comprising:
- assuming that a filtered back projection reconstruction of a computed tomography image is available;
- acquiring a deviate of a multivariate random variable computed tomography data set;
- estimating a filtered back projection reconstruction of the image;
- identifying the filtered back projection reconstruction as a deviate of a multivariate random variable; and
- generating a maximum a posteriori estimate for the filtered back projection reconstruction.

19. The computer-readable medium of claim 18, wherein the computer-executable instructions, when executed by the processor, implement the method further comprising estimating the filtered back projection reconstruction for subjects that extend beyond a field of view for a computed tomography device used to acquire the computed tomography image.

20. The computer-readable medium of claim 18, wherein the computer-executable instructions, when executed by the processor, implement the method further comprising calculating a covariance matrix for the reconstruction by computing a subset of rows of the covariance matrix using reference pixels in the image that correspond to a downsampled version of the reconstruction, and interpolating a remainder of the rows.

\* \* \* \* \*